United States Patent
Maschino

(10) Patent No.: US 8,204,603 B2
(45) Date of Patent: Jun. 19, 2012

(54) BLOCKING EXOGENOUS ACTION POTENTIALS BY AN IMPLANTABLE MEDICAL DEVICE

(75) Inventor: Steven E. Maschino, Seabrook, TX (US)

(73) Assignee: Cyberonics, Inc., Houston, TX (US)

( * ) Notice: Subject to any disclaimer, the term of this patent is extended or adjusted under 35 U.S.C. 154(b) by 1090 days.

(21) Appl. No.: 12/109,467

(22) Filed: Apr. 25, 2008

(65) Prior Publication Data

US 2009/0270943 A1    Oct. 29, 2009

(51) Int. Cl.
*A63B 21/00* (2006.01)
*A61N 1/18* (2006.01)

(52) U.S. Cl. .............. 607/74; 607/63; 607/66; 607/139; 607/148

(58) Field of Classification Search .................. 607/63, 607/66, 74, 139, 148
See application file for complete search history.

(56) References Cited

U.S. PATENT DOCUMENTS

| | | |
|---|---|---|
| 3,760,812 A | 9/1973 | Timm et al. |
| 3,796,221 A | 3/1974 | Hagfors |
| 4,107,469 A | 8/1978 | Jenkins |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara ........................ 128/784 |
| 4,577,316 A | 3/1986 | Schiff |
| 4,590,946 A | 5/1986 | Loeb |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zabara ........................ 128/421 |
| 4,793,353 A | 12/1988 | Borkan |
| 4,821,723 A | 4/1989 | Baker, Jr. et al. ........ 128/419 D |
| 4,867,164 A | 9/1989 | Zabara ........................ 128/421 |

(Continued)

FOREIGN PATENT DOCUMENTS

CA    2339971    6/2004

(Continued)

OTHER PUBLICATIONS

Woo et al., *Bull. L.A. Neurolog. Soc.* 31(2):87-94 (1964).

(Continued)

*Primary Examiner* — Carl H Layno
*Assistant Examiner* — Natasha Patel
(74) *Attorney, Agent, or Firm* — Cyberonics, Inc.

(57) ABSTRACT

An implantable medical device (IMD) to treat a medical condition in a patient comprises an electrical signal generator; a cathode and an anode operatively coupled to the electrical signal generator and a cranial nerve of the patient; and a third electrode operatively coupled to the electrical signal generator and implanted within the patient's body; wherein the electrical signal generator is capable of generating and delivering at least one electrical signal effective at the anode to block at least a sufficient portion of action potentials induced by the at least one electrical signal in the cranial nerve proximate the cathode to reduce a side effect of said induced action potentials.

21 Claims, 10 Drawing Sheets

U.S. PATENT DOCUMENTS

| | | | |
|---|---|---|---|
| 4,920,979 A | 5/1990 | Bullara | |
| 4,949,721 A | 8/1990 | Toriu et al. | |
| 4,977,985 A | 12/1990 | Wells et al. | |
| 4,979,511 A | 12/1990 | Terry, Jr. | 128/642 |
| 5,025,807 A | 6/1991 | Zabara | 128/421 |
| 5,081,987 A | 1/1992 | Nigam | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | 128/419 R |
| 5,205,285 A | 4/1993 | Baker, Jr. | 128/432 R |
| 5,215,086 A | 6/1993 | Terry, Jr. et al. | 128/421 |
| 5,222,494 A | 6/1993 | Baker, Jr. | |
| 5,231,988 A | 8/1993 | Wernicke et al. | 128/421 |
| 5,235,980 A | 8/1993 | Varrichio et al. | |
| 5,263,480 A | 11/1993 | Wernicke et al. | 607/118 |
| 5,269,303 A | 12/1993 | Wernicke et al. | 607/45 |
| 5,299,569 A | 4/1994 | Wernicke et al. | 607/45 |
| 5,330,507 A | 7/1994 | Schwartz | |
| 5,330,515 A | 7/1994 | Rutecki et al. | 607/46 |
| 5,334,221 A | 8/1994 | Bardy | |
| 5,335,657 A | 8/1994 | Terry, Jr. et al. | 607/45 |
| 5,354,320 A | 10/1994 | Schaldach et al. | |
| 5,411,531 A | 5/1995 | Hill et al. | |
| 5,411,540 A | 5/1995 | Edell et al. | |
| 5,423,872 A | 6/1995 | Cigaina | |
| 5,507,784 A | 4/1996 | Hill et al. | |
| 5,522,862 A | 6/1996 | Testerman et al. | |
| 5,522,865 A | 6/1996 | Schulman et al. | |
| 5,531,778 A | 7/1996 | Maschino et al. | 607/118 |
| 5,540,730 A | 7/1996 | Terry, Jr. et al. | |
| 5,540,734 A | 7/1996 | Zabara | |
| 5,571,150 A | 11/1996 | Wernicke et al. | 607/72 |
| 5,601,617 A | 2/1997 | Loeb et al. | |
| 5,611,350 A | 3/1997 | John | |
| 5,645,570 A | 7/1997 | Corbucci | |
| 5,651,378 A | 7/1997 | Matheny et al. | |
| 5,658,318 A | 8/1997 | Stroetmann et al. | |
| 5,690,681 A | 11/1997 | Geddes et al. | |
| 5,690,688 A | 11/1997 | Noren et al. | |
| 5,690,691 A | 11/1997 | Chen et al. | |
| 5,700,282 A | 12/1997 | Zabara | |
| 5,702,428 A | 12/1997 | Tippey et al. | |
| 5,702,429 A | 12/1997 | King | |
| 5,707,400 A | 1/1998 | Terry, Jr. et al. | 607/44 |
| 5,755,750 A | 5/1998 | Petruska et al. | |
| 5,792,212 A | 8/1998 | Weijand | |
| 5,800,474 A | 9/1998 | Benabid et al. | |
| 5,814,092 A | 9/1998 | King | |
| 5,836,994 A | 11/1998 | Bourgeois | |
| 5,861,014 A | 1/1999 | Familoni | |
| 5,913,882 A | 6/1999 | King | |
| 5,916,239 A | 6/1999 | Geddes et al. | 607/14 |
| 5,928,272 A | 7/1999 | Adkins et al. | |
| 5,941,906 A | 8/1999 | Barreras, Sr. et al. | |
| 5,995,868 A | 11/1999 | Dorfmeister et al. | |
| 6,002,966 A | 12/1999 | Loeb et al. | |
| 6,016,449 A | 1/2000 | Fischell et al. | |
| 6,041,258 A | 3/2000 | Cigaina et al. | |
| 6,067,470 A | 5/2000 | Mower | 607/5 |
| 6,083,249 A | 7/2000 | Familoni | |
| 6,101,412 A | 8/2000 | Duhaylongsod | |
| 6,104,955 A | 8/2000 | Bourgeois | |
| 6,104,956 A | 8/2000 | Naritoku et al. | |
| 6,115,628 A | 9/2000 | Stadler et al. | |
| 6,132,361 A | 10/2000 | Epstein et al. | |
| 6,141,590 A | 10/2000 | Renirie et al. | |
| 6,161,044 A | 12/2000 | Silverstone | |
| 6,167,311 A | 12/2000 | Rezai | |
| 6,175,764 B1 | 1/2001 | Loeb et al. | |
| 6,188,929 B1 | 2/2001 | Giordano | |
| 6,219,580 B1 | 4/2001 | Faltys et al. | |
| 6,221,908 B1 | 4/2001 | Kilgard et al. | |
| 6,238,423 B1 | 5/2001 | Bardy | |
| 6,249,704 B1 | 6/2001 | Maltan et al. | |
| 6,253,109 B1 | 6/2001 | Gielen | |
| 6,266,564 B1 | 7/2001 | Hill et al. | |
| 6,269,270 B1 | 7/2001 | Boveja | |
| 6,295,472 B1 | 9/2001 | Rubinstein et al. | |
| 6,304,775 B1 | 10/2001 | Iasemidis et al. | |
| 6,308,102 B1 | 10/2001 | Sieracki et al. | |
| 6,324,421 B1 | 11/2001 | Stadler et al. | |
| 6,327,503 B1 | 12/2001 | Familoni | |
| 6,339,725 B1 | 1/2002 | Naritoku et al. | |
| 6,341,236 B1 | 1/2002 | Osorio et al. | |
| 6,353,762 B1 | 3/2002 | Baudino et al. | |
| 6,356,788 B2 | 3/2002 | Boveja | |
| 6,358,203 B2 | 3/2002 | Bardy | |
| 6,366,813 B1 | 4/2002 | DiLorenzo | |
| 6,366,814 B1 | 4/2002 | Boveja et al. | |
| 6,374,140 B1 | 4/2002 | Rise | |
| 6,381,493 B1 | 4/2002 | Stadler et al. | |
| 6,381,496 B1 | 4/2002 | Meadows et al. | |
| 6,381,499 B1 | 4/2002 | Taylor et al. | |
| 6,418,344 B1 | 7/2002 | Rezai et al. | |
| 6,425,852 B1 | 7/2002 | Epstein et al. | |
| 6,438,423 B1 | 8/2002 | Rezai et al. | |
| 6,449,512 B1 | 9/2002 | Boveja | |
| 6,453,199 B1 | 9/2002 | Kobozev | |
| 6,459,936 B2 | 10/2002 | Fischell et al. | |
| 6,463,328 B1 | 10/2002 | John | |
| 6,466,822 B1 | 10/2002 | Pless | |
| 6,473,639 B1 | 10/2002 | Fischell et al. | |
| 6,473,644 B1 | 10/2002 | Terry, Jr. et al. | |
| 6,477,417 B1 | 11/2002 | Levine | |
| 6,477,418 B2 | 11/2002 | Plicchi et al. | |
| 6,480,743 B1 | 11/2002 | Kirkpatrick et al. | |
| 6,484,132 B1 | 11/2002 | Hively et al. | |
| 6,487,446 B1 | 11/2002 | Hill et al. | |
| 6,505,074 B2 | 1/2003 | Boveja et al. | |
| 6,522,928 B2 | 2/2003 | Whitehurst et al. | |
| 6,532,388 B1 | 3/2003 | Hill et al. | |
| 6,549,804 B1 | 4/2003 | Osorio et al. | |
| 6,556,868 B2 | 4/2003 | Naritoku et al. | |
| 6,564,102 B1 | 5/2003 | Boveja | |
| 6,565,503 B2 | 5/2003 | Leysieffer et al. | |
| 6,579,280 B1 | 6/2003 | Kovach et al. | |
| 6,587,719 B1 | 7/2003 | Barrett et al. | 607/2 |
| 6,587,724 B2 | 7/2003 | Mann | |
| 6,587,726 B2 | 7/2003 | Lurie et al. | |
| 6,587,727 B2 | 7/2003 | Osorio et al. | |
| 6,591,138 B1 | 7/2003 | Fischell et al. | |
| 6,594,524 B2 | 7/2003 | Esteller et al. | |
| 6,600,953 B2 | 7/2003 | Flesler et al. | |
| 6,609,025 B2 | 8/2003 | Barrett et al. | 607/2 |
| 6,609,030 B1 | 8/2003 | Rezai et al. | |
| 6,609,031 B1 | 8/2003 | Law et al. | |
| 6,610,713 B2 | 8/2003 | Tracey | |
| 6,611,715 B1 | 8/2003 | Boveja | |
| 6,612,983 B1 | 9/2003 | Marchal | |
| 6,615,081 B1 | 9/2003 | Boveja | |
| 6,615,084 B1 | 9/2003 | Cigaina | |
| 6,615,085 B1 | 9/2003 | Boveja | |
| 6,622,038 B2 | 9/2003 | Barrett et al. | |
| 6,622,041 B2 | 9/2003 | Terry, Jr. et al. | 607/9 |
| 6,622,047 B2 | 9/2003 | Barrett et al. | |
| 6,628,987 B1 | 9/2003 | Hill et al. | |
| 6,656,960 B2 | 12/2003 | Puskas | |
| 6,662,053 B2 | 12/2003 | Borkan | |
| 6,668,191 B1 | 12/2003 | Boveja | |
| 6,671,547 B2 | 12/2003 | Lyster et al. | |
| 6,671,555 B2 | 12/2003 | Gielen et al. | |
| 6,671,556 B2 | 12/2003 | Osorio et al. | |
| 6,684,104 B2 | 1/2004 | Gordon et al. | |
| 6,684,105 B2 | 1/2004 | Cohen et al. | |
| 6,690,973 B2 | 2/2004 | Hill et al. | |
| 6,690,974 B2 | 2/2004 | Archer et al. | |
| 6,708,064 B2 | 3/2004 | Rezai | |
| 6,721,603 B2 | 4/2004 | Zabara et al. | |
| 6,731,979 B2 | 5/2004 | MacDonald | |
| 6,731,986 B2 | 5/2004 | Mann | |
| 6,754,536 B2 | 6/2004 | Swoyer et al. | |
| 6,760,626 B1 | 7/2004 | Boveja | |
| 6,764,498 B2 | 7/2004 | Mische | |
| 6,768,969 B1 | 7/2004 | Nikitin et al. | |
| 6,775,573 B2 | 8/2004 | Schuler et al. | |
| 6,793,670 B2 | 9/2004 | Osorio et al. | |

| Patent/Publication | Date | Inventor |
|---|---|---|
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,054,686 B2 | 5/2006 | MacDonald |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,340,302 B1 | 3/2008 | Falkenberg et al. |
| 2003/0181954 A1 | 9/2003 | Rezai |
| 2003/0181958 A1 | 9/2003 | Dobak, III |
| 2003/0181959 A1 | 9/2003 | Dobak, III |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0036377 A1 | 2/2004 | Mezinis |
| 2004/0039424 A1 | 2/2004 | Merritt et al. |
| 2004/0088024 A1 | 5/2004 | Firlik et al. |
| 2004/0111139 A1 | 6/2004 | McCreery |
| 2004/0112894 A1 | 6/2004 | Varma |
| 2004/0122484 A1 | 6/2004 | Hatlestad et al. |
| 2004/0122485 A1 | 6/2004 | Stahmann et al. |
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199212 A1 | 10/2004 | Fischell et al. |
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0249416 A1 | 12/2004 | Yun et al. |
| 2004/0254612 A1* | 12/2004 | Ezra et al. ............... 607/5 |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai et al. |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathur |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai |
| 2005/0107858 A1 | 5/2005 | Bluger |
| 2005/0113705 A1 | 5/2005 | Fischell et al. |
| 2005/0113744 A1 | 5/2005 | Donoghue et al. |
| 2005/0119703 A1 | 6/2005 | DiLorenzo |
| 2005/0124901 A1 | 6/2005 | Misczynski et al. |
| 2005/0131467 A1 | 6/2005 | Boveja |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0131506 A1 | 6/2005 | Rezai et al. |
| 2005/0137480 A1 | 6/2005 | Alt et al. |
| 2005/0143781 A1 | 6/2005 | Carbunaru et al. |
| 2005/0143786 A1 | 6/2005 | Boveja |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0261542 A1 | 11/2005 | Riehl |
| 2005/0267550 A1 | 12/2005 | Hess et al. |
| 2005/0272280 A1 | 12/2005 | Osypka |
| 2005/0277872 A1 | 12/2005 | Colby et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |

| | | |
|---|---|---|
| 2005/0288760 A1 | 12/2005 | Machado et al. |
| 2006/0009815 A1 | 1/2006 | Boveja et al. |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja et al. |
| 2006/0079936 A1 | 4/2006 | Boveja et al. |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0100667 A1 | 5/2006 | Machado et al. |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0259098 A1* | 11/2006 | Erickson .................. 607/61 |
| 2006/0264730 A1 | 11/2006 | Stivoric et al. |
| 2006/0265018 A1 | 11/2006 | Smith et al. |
| 2006/0271409 A1 | 11/2006 | Rosenfeld et al. |
| 2006/0293720 A1 | 12/2006 | DiLorenzo |
| 2007/0027486 A1 | 2/2007 | Armstrong |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand |
| 2007/0073150 A1 | 3/2007 | Gopalsami et al. |
| 2007/0073346 A1 | 3/2007 | Corbucci |
| 2007/0073355 A1 | 3/2007 | Dilorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson |
| 2007/0100278 A1 | 5/2007 | Frei et al. |
| 2007/0100397 A1 | 5/2007 | Seeberger et al. |
| 2007/0100398 A1 | 5/2007 | Sloan |
| 2007/0112393 A1 | 5/2007 | Gliner |
| 2007/0123946 A1 | 5/2007 | Masoud |
| 2007/0135855 A1 | 6/2007 | Foshee et al. |
| 2007/0142862 A1 | 6/2007 | Dilorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | Dilorenzo et al. |
| 2007/0156179 A1 | 7/2007 | Karashurov |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0179534 A1 | 8/2007 | Firlik et al. |
| 2007/0179584 A1 | 8/2007 | Gliner |
| 2007/0203548 A1 | 8/2007 | Pawelzik et al. |
| 2007/0208212 A1 | 9/2007 | DiLorenzo |
| 2007/0208390 A1 | 9/2007 | Von Arx et al. |
| 2007/0213785 A1 | 9/2007 | Osorio et al. |
| 2007/0233192 A1 | 10/2007 | Craig |
| 2007/0233193 A1 | 10/2007 | Craig .................. 607/2 |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0250130 A1 | 10/2007 | Ball et al. |
| 2007/0250145 A1 | 10/2007 | Kraus et al. |
| 2007/0255147 A1 | 11/2007 | Drew et al. |
| 2007/0255155 A1 | 11/2007 | Drew et al. |
| 2007/0255330 A1 | 11/2007 | Lee et al. |
| 2007/0255337 A1 | 11/2007 | Lu |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | Dilorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0039895 A1 | 2/2008 | Fowler et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |

| | | | |
|---|---|---|---|
| 2008/0161882 | A1 | 7/2008 | Firlik et al. |
| 2008/0183096 | A1 | 7/2008 | Snyder et al. |
| 2008/0183097 | A1 | 7/2008 | Leyde et al. |
| 2008/0183245 | A1 | 7/2008 | Van Oort et al. |
| 2008/0195175 | A1 | 8/2008 | Balzer et al. |
| 2008/0200925 | A1 | 8/2008 | Johnson et al. |
| 2008/0208013 | A1 | 8/2008 | Zhang et al. |
| 2008/0208074 | A1 | 8/2008 | Snyder et al. |
| 2008/0208285 | A1 | 8/2008 | Fowler et al. |
| 2008/0208291 | A1 | 8/2008 | Leyde et al. |
| 2008/0208781 | A1 | 8/2008 | Snyder |
| 2008/0215112 | A1 | 9/2008 | Firlik et al. |
| 2008/0215114 | A1 | 9/2008 | Stuerzinger et al. |
| 2008/0221644 | A1 | 9/2008 | Vallapureddy et al. |
| 2008/0234598 | A1 | 9/2008 | Snyder et al. |
| 2008/0249591 | A1 | 10/2008 | Gaw et al. |
| 2008/0255582 | A1 | 10/2008 | Harris |
| 2009/0054795 | A1 | 2/2009 | Misczynski et al. |
| 2009/0076567 | A1 | 3/2009 | Fowler et al. |

FOREIGN PATENT DOCUMENTS

| | | | |
|---|---|---|---|
| EP | 0402683 | A2 | 12/1990 |
| EP | 0713714 | A2 | 5/1996 |
| EP | 1647300 | A2 | 2/1998 |
| EP | 1070518 | A2 | 1/2001 |
| EP | 1120130 | A2 | 1/2001 |
| EP | 1145736 | A2 | 10/2001 |
| EP | 1595497 | A1 | 5/2004 |
| EP | 1486232 | A2 | 12/2004 |
| GB | 2026870 | A | 2/1980 |
| GB | 2079610 | A | 1/1982 |
| WO | 9302744 | A1 | 8/1992 |
| WO | 9417771 | A2 | 2/1998 |
| WO | 9825688 | A1 | 6/1998 |
| WO | 0040143 | A1 | 12/1999 |
| WO | 0064336 | A1 | 11/2000 |
| WO | 0105467 | A1 | 1/2001 |
| WO | 0108749 | A1 | 2/2001 |
| WO | 0064336 | C2 | 6/2002 |
| WO | 03076010 | A1 | 9/2003 |
| WO | 03085546 | A1 | 10/2003 |
| WO | 2004036377 | A2 | 4/2004 |
| WO | 2004064918 | A1 | 8/2004 |
| WO | 2004071575 | A1 | 8/2004 |
| WO | 2004075982 | A1 | 9/2004 |
| WO | 2004112894 | A1 | 12/2004 |
| WO | 2005007120 | A2 | 1/2005 |
| WO | 2005007232 | A2 | 1/2005 |
| WO | 2005028026 | A1 | 3/2005 |
| WO | 2005053788 | A1 | 6/2005 |
| WO | 2005067599 | A2 | 7/2005 |
| WO | 2004069330 | A1 | 8/2005 |
| WO | 2005101282 | A2 | 10/2005 |
| WO | 2006014760 | A1 | 2/2006 |
| WO | 2006019822 | A2 | 2/2006 |
| WO | 2006050144 | A1 | 5/2006 |
| WO | 2006122148 | A2 | 11/2006 |
| WO | 2007066343 | A2 | 6/2007 |
| WO | 2007072425 | A2 | 6/2007 |
| WO | 2007124126 | A2 | 11/2007 |
| WO | 2007124190 | A2 | 11/2007 |
| WO | 2007124192 | A1 | 11/2007 |
| WO | 2007142523 | A1 | 12/2007 |

OTHER PUBLICATIONS

Lockard et al., "Feasibility and Safety of Vagal Stimulation in Monkey Model;" Epilepsia, vol. 31 (Supp. 2) (1990), pp. S20-S26.

Bachman, D.,S. et al.; "Effects of Vagal Volleys and Serotonin on Units of Cingulate Cortex in Monkeys;" Brain Research, vol. 130 (1977). pp. 253-269.

Terry et al.; "The Implantable Neurocybernetic Prosthesis System", Pacing and Clinical Electrophysiology, vol. 14, No. 1 (Jan. 1991), pp. 86-93.

Bohning, D.E., et al.; "Feasibility of Vagus Nerve Stimulation—Synchronized Blood Oxygenation Level-Dependent Functional MRI;" A Journal of Clinical and Laboratory Research: Investigative Radiology; vol. 36, No. 8 (Aug. 2001); pp. 470-479.

Boon, Paul, et al.; "Programmed and Magnet-Induced Vagus Nerve Stimulation for Refractory Epilepsy;" Journal of Clinical Neurophysiology vol. 18 No. 5; (2001); pp. 402-407.

Clark, K.B., et al.; "Posttraining Electrical Stimulation of Vagal Afferents with Concomitant Vagal Efferent Inactivation Enhances Memory Storage Processes in the Rat;" Neurobiology of Learning and Memory, vol. 70, 364-373 (1998).

Clark, K.B., et al.; "Enhanced Recognition Memory Following Vagus Nerve Stimulation in Human Subjects;" Nature Neuroscience, vol. 2, No. 1, (Jan. 1999) pp. 93-98.

DeGiorgo, Christopher M., et al.; "Vagus Nerve Stimulation: Analysis of Device Parameters in 154 Patients During the Long-Term XE5 Study;" Epilepsia, vol. 42, No. 8; pp. 1017-1020 (2001).

Devous, Michael D., et al.; "Effects of Vagus Nerve Stimulation on Regional Cerebral Blood Flow in Treatment-Resistant Depression;" National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.

Dodrill, Ph.D., et al.; "Effects of Vagal Nerve Stimulation on Cognition and Quality of Life in Epilepsy;" Epilepsy and Behavior, vol. 2 (2001); pp. 46-53.

Fanselow, E. E., et al.; "Reduction of Pentylenetetrazole-Induced Seizure Activity in Awake Rats by Seizure-Triggered Trigeminal Nerve Stimulation;" The Journal of Neuroscience, vol. 20, No. 21; (Nov. 2000); pp. 8160-8168.

George, M.S., et al.; "Open Trial of VNS Therapy in Severe Anxiety Disorders;" 156th American Psychiatric Association Annual Meeting; May 17-22, 2003.

George, M.S., et al.; "Vagus Nerve Stimulation: A New Tool for Brain Research and Therapy;" Society of Biological Psychiatry vol. 47 (2000) pp. 287-295.

Hallowitz, R.A., et al.; "Effects of Vagal Volleys on Units of Intralaminar and Juxtalaminar Thalamic Nuclei in Monkeys;" Brain Research, vol. 130 (1977), pp. 271-286.

Henry, MD, T.R.; "Therapeutic Mechanisms of Vagus Nerve Stimulation" Neurology, vol. 59 Suppl. 4 (Sep. 2002); pp. S3-S14.

King, M.D., "Effects of Short-Term Vagus Nerve Stimulation (VNS) on FOS Expression in Rat Brain Nuclei" 58th Annual Scientific Convention of the Society of Biological Psychiatry, (May 2003).

Klapper, M.D., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).

Koo, B., "EEG Changes With Vagus Nerve Stimulation" Journal of Clinical Neurophysiology, vol. 18 No. 5 (Sep. 2001); pp. 434-441.

Labar, D., "Vagus Nerve Stimulation for 1 Year in 269 patients on Unchanged Antiepilectic Drugs" Seizure vol. 13, (2004) pp. 392-398.

Liebman, K.M. et al.; "Improvement in Cognitive Function After Vagal Nerve Stimulator Implantation;" Epilepsia, vol. 39, Suppl. 6 (1998) 1 page.

Malow, B.A., et al.; "Vagus Nerve Stimulation Reduces Daytime Sleepiness in Epilepsy Patients" Neurology 57 (2001) pp. 879-884.

McClintock, P., Can Noise Actually Boost Brain Power Physics World Jul. 2002; pp. 20-21.

Mori, T., et al.; "Noise-Induced Entrainment and Stochastic Resonance in Human Brain Waves" Physical Review Letters vol. 88, No. 21 (May 2002); pp. 218101-1-218101-4.

Rugg-Gunn, F.J., et al.; "Cardiac Arrhythmias in Focal Epilepsy: a Prospective Long-Term Study" www.thelancet.com vol. 364 (2004) pp. 2212-2219.

Rutecki, P.; "Anatomical, Physiological, and Theoretical Basis for the Antiepileptic Effect of Vagus Nerve Stimulation" Epilepsia, vol. 31 Suppl. 2; S1-S6 (1990).

Sahin, M.; et al.; "Improved Nerve Cuff Electrode Recordings with Subthreshold Anodic Currents;" IEEE Transactions on Biomedical Engineering, vol. 45, No. 8 (Aug. 1998) pp. 1044-1050.

Schachter, S.C., et al.; "Progress in Epilepsy Research: Vagus Nerve Stimulation;" Epilepsia, vol. 39, No. 7 (1998) pp. 677-686.

Tatum, W.O., et al.; "Ventricular Asystole During Vagus Nerve Stimulation for Epilepsy in Humans" American Academy of Neuroloygy (1999) p. 1267 (See also pp. 1117, 1166, and 1265).

Tatum, W.O., et al.; "Vagus Nerve Stimulation and Drug Reduction" Neurology, vol. 56, No. 4 (Feb. 2001) pp. 561-563.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Valdes-Cruz, A., et al.; "Chronic Stimulation of the Cat Vagus Nerve Effect on Sleep and Behavior" Progress in Neuro-Psychopharmacology & Biological Psychiatry, vol. 26 (2002) pp. 113-118.

Vonck et al. "The Mechanism of Action of Vagus Nerve Stimulation for Refractory Epilepsy", Journal of Clinical Neurophysiology, vol. 18(5) (2001), pp. 394-401.

Ward, H., M.D., et al.; "Treatment-Refractory Obsessive-Compulsive Disorder: Potential Benefit of VNS Therapy" 23rd Annual Conference of the Anxiety Disorders Association of America (2007).

Zabara, J. "Inhibition of Experimental Seizures in Canines by Repetivie Vagal Stimulation" Epilepsia vol. 33, No. 6 (1992); pp. 1005-1012.

Craig, A.D. (BUD); "Distribution of Trigeminothalamic and Spinothalamic Lamina I Terminations in the Macaque Monkey;" The Journal of Comparative Neurology, vol. 477, pp. 119-148 (2004).

Harry, J.D., et al.; "Balancing Act: Noise is the Key to Restoring the Body's Sense of Equilibrium;" IEEE Spectrum (Apr. 2005)pp. 37-41.

Henry, T.R., et al.; "Brain Blood-Flow Alterations Induced by Therapeutic Vagus Nerve Stimulation in Partial Epilepsy: I. Acute Effects at High and Low Levels of Stimulation;" Epilepsia vol. 39, No. 9; pp. 984-990 (1998).

Woodbury, et al., "Vagal Stimulation Reduces the Severity of Maximal Electroshock Seizures in Intact Rats. Use of a Cuff Electrode for Stimulating and Recording"; Pacing and Clinical Electrophysiology, vol. 14 (Jan. 1991), pp. 94-107.

* cited by examiner

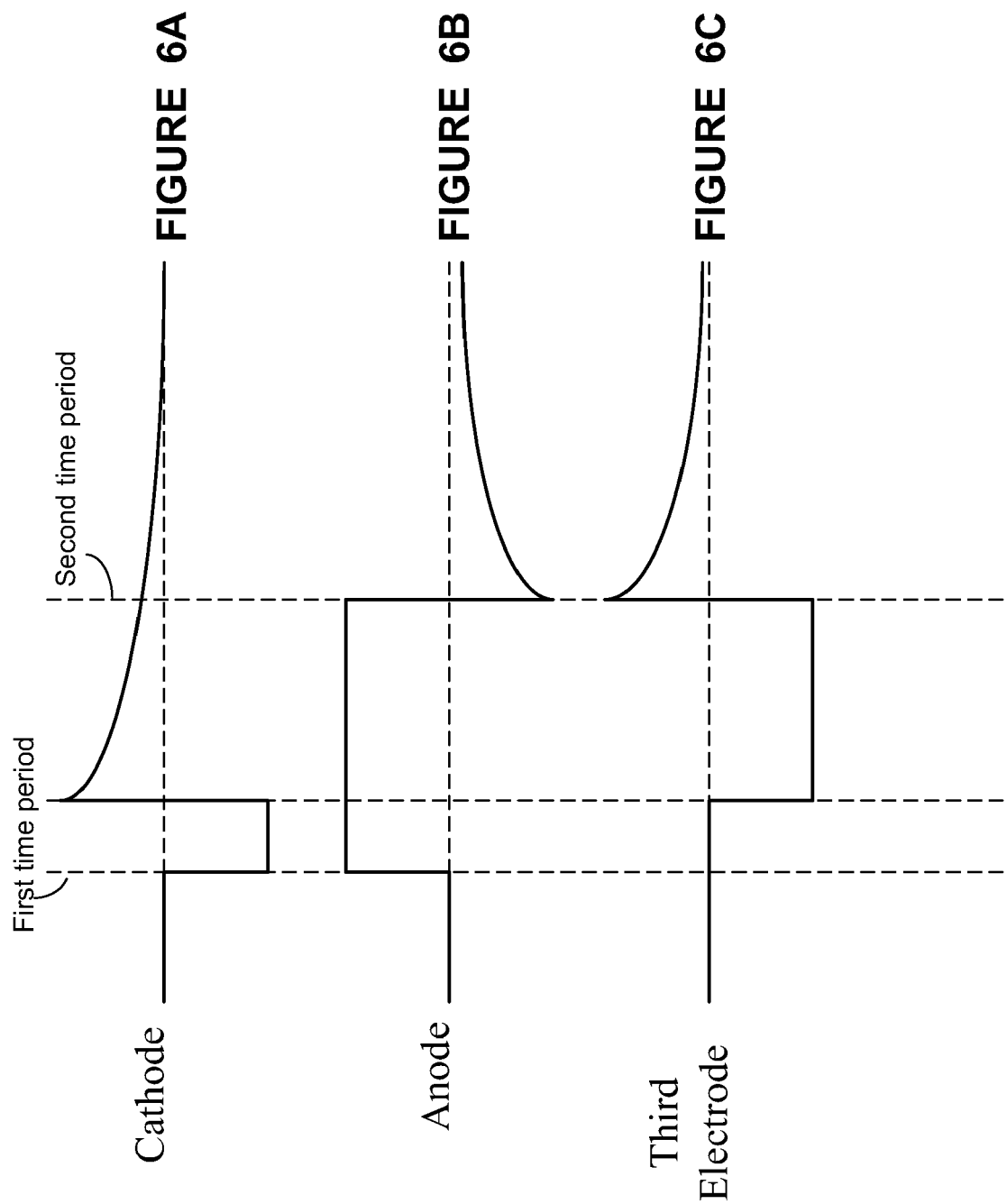

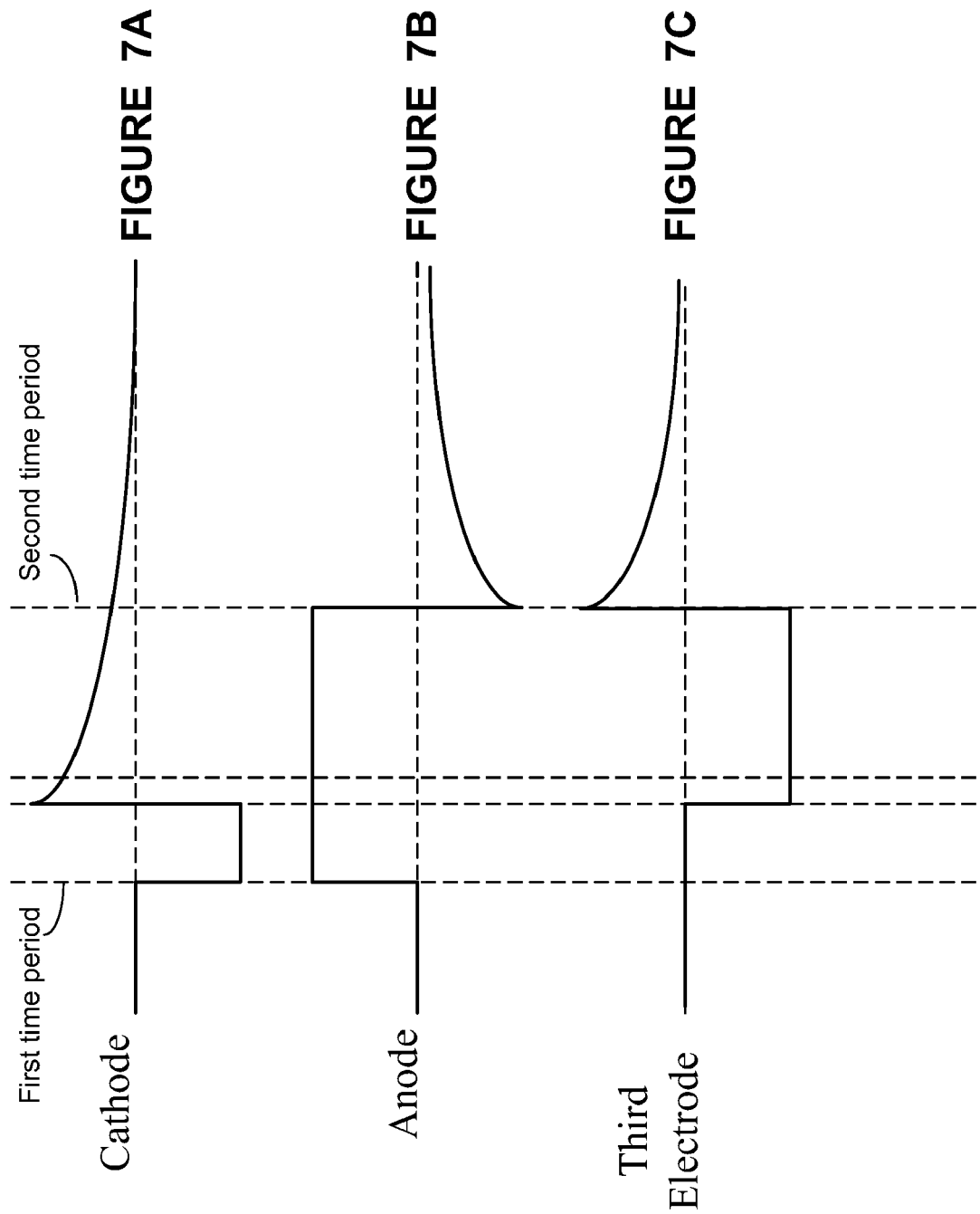

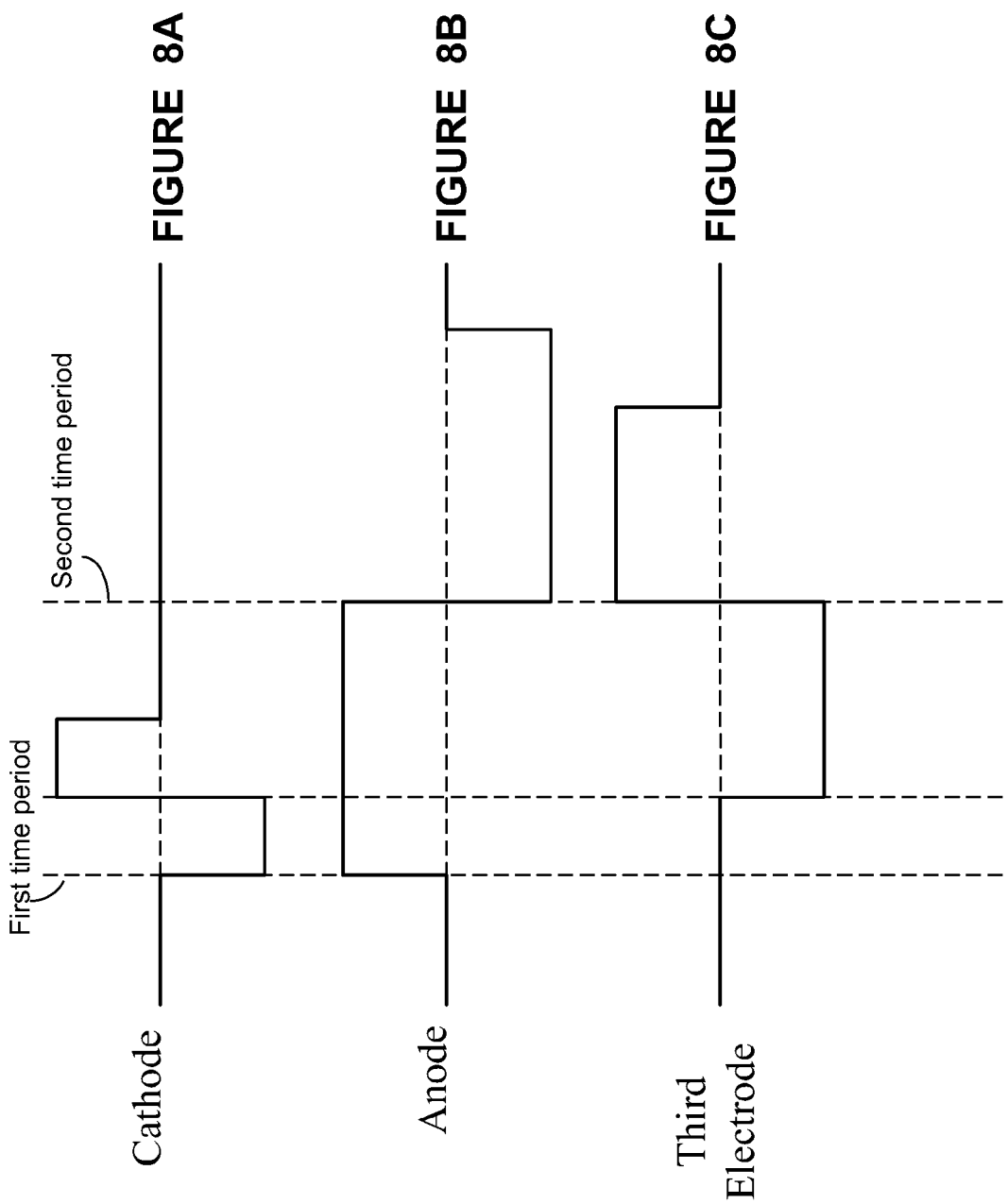

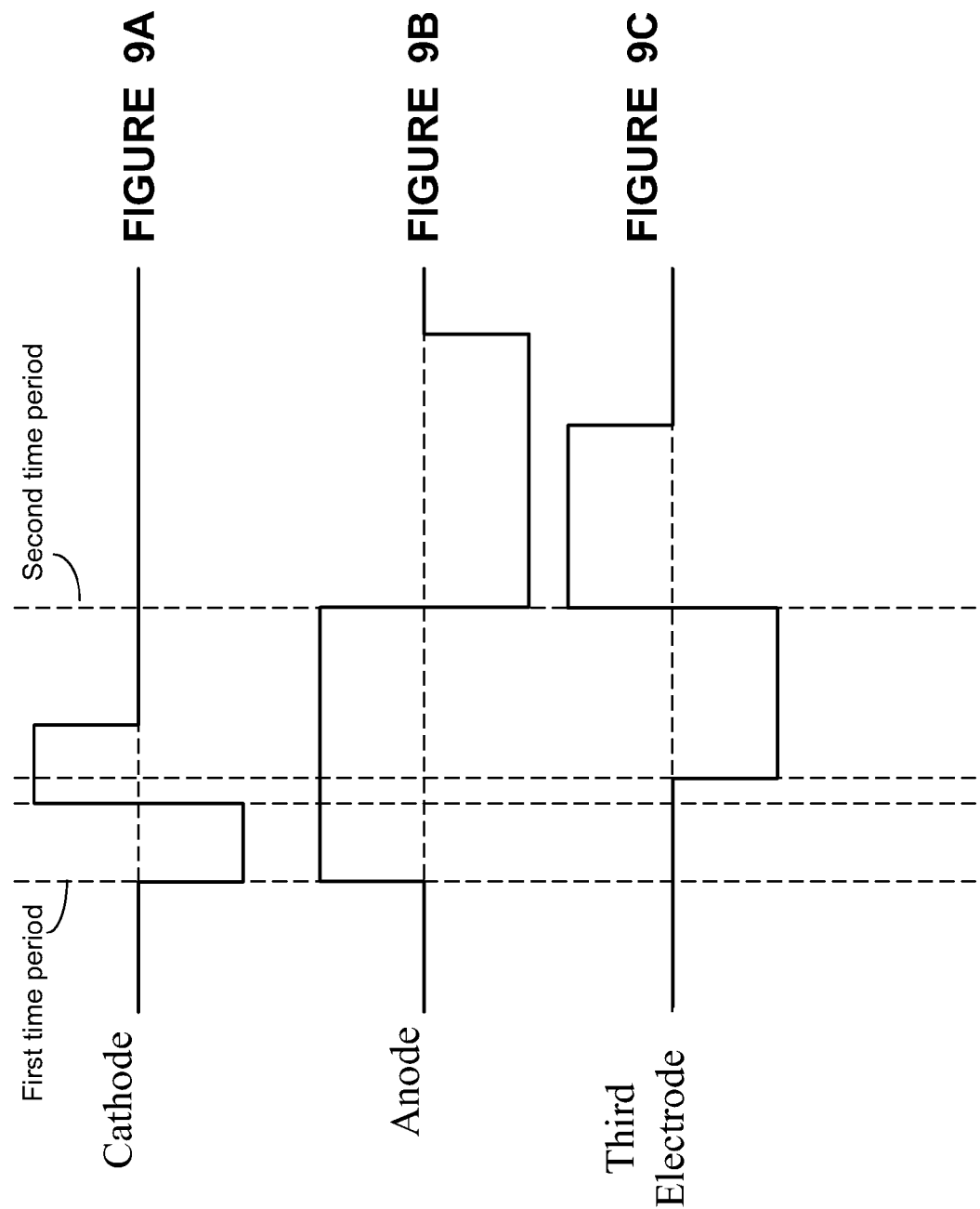

BLOCKING EXOGENOUS ACTION POTENTIALS BY AN IMPLANTABLE MEDICAL DEVICE

BACKGROUND OF THE INVENTION

1. Field of the Invention

This invention relates generally to medical devices, and, more particularly, to methods, apparatus, and systems for performing electrical signal therapy by a medical device.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. Nos. 4,702,254, 4,867,164, and 5,025,807 to Dr. Jacob Zabara, which are hereby incorporated in this specification in their entirety by reference.

More generally, the endogenous electrical activity (i.e., activity attributable to the natural functioning of the patient's own body) of a neural structure of a patient may be modulated in a variety of ways. In particular, the electrical activity may be modulated by exogenously applied (i.e., from a source other than the patient's own body) electrical, chemical, or mechanical signals applied to the neural structure. The modulation (hereinafter referred to generally as "neurostimulation" or "neuromodulation") may involve the induction of afferent action potentials, efferent action potentials, or both, in the neural structure, and may also involve blocking or interrupting the transmission of endogenous electrical activity traveling along the nerve.

Electrical signal therapy or electrical modulation of a neural structure (also known as "electrical signal therapy") refers to the application of an exogenous therapeutic electrical signal (as opposed to a chemical or mechanical signal), to the neural structure. Electrical signal therapy may be provided by implanting an electrical device underneath the skin of a patient and delivering an electrical signal to a nerve such as a cranial nerve. In some cases, the electrical signal therapy may involve performing a detection step, with the electrical signal being delivered in response to a detected body parameter. This type of stimulation is generally referred to as "active," "feedback," or "triggered" stimulation. Alternatively, the system may operate without a detection system once the patient has been diagnosed with epilepsy (or another medical condition), and may periodically apply a series of electrical pulses to the nerve (e.g., a cranial nerve such as a vagus nerve) intermittently throughout the day, or over another predetermined time interval. This type of stimulation is generally referred to as "passive," "non-feedback," or "prophylactic," stimulation. It is also possible to combine active and passive stimulation by using a programmed, intermittent signal operating according to a programmed duty cycle, and a detection system that operates when an event, such as an elevated heart rate, is detected. The stimulation may be applied by an implantable medical device that is implanted within the patient's body.

When inducing action potentials in a cranial nerve, action potentials will propagate in both the afferent direction (toward the brain) and efferent direction (toward a body structure innervated by the cranial nerve). If it is desired to provide electrical signal therapy acting on a structure in the brain, the propagation of efferent action potentials may lead to side effects in the innervated body structure. For example, when an implantable medical device induces action potentials in the vagus nerve in the neck, efferent action potentials may travel down the vagus nerve and the recurrent laryngeal nerve (a branch of the vagus nerve), stimulating muscle activity proximate the larynx. As a result, a patient may experience unwelcome modulation of the vocal cords, or other side effects, resulting in impaired speech volume, timbre, or other activity.

Therefore, a need exists for apparatus and methods for performing electrical signal stimulation of the brain via a cranial nerve with reduced side effects in body structures innervated by the cranial nerve.

SUMMARY OF THE INVENTION

In one aspect, the present invention relates to an implantable medical device (IMD) to treat a medical condition in a patient, comprising an electrical signal generator; a cathode and an anode operatively coupled to the electrical signal generator and a cranial nerve of the patient; and a third electrode operatively coupled to the electrical signal generator and implanted within the patient's body; wherein the electrical signal generator is capable of generating and delivering at least one electrical signal effective at the anode to block at least a sufficient portion of action potentials induced by the at least one electrical signal in the cranial nerve proximate the cathode to reduce a side effect of said induced action potentials.

In one aspect, the present invention relates to a method of treating a medical condition in a patient using an implantable medical device, comprising providing an electrical signal generator, coupling at least a cathode and an anode to a cranial nerve of the patient and to the electrical signal generator, providing at least a third electrode implanted within the patient's body and coupled to the electrical signal generator, generating a first electrical signal with the electrical signal generator, and delivering at least one electrical signal effective at the anode to block at least a sufficient portion of action potentials induced by the at least one electrical signal in the cranial nerve proximate the cathode to reduce a side effect of said induced action potentials.

In one aspect, the present invention relates to, in a method of neuromodulation effected by delivery of an exogenous electrical signal, using at least two electrodes, to a cranial nerve of a patient, the improvement comprising providing an electrical signal generator, coupling at least a cathode and an anode to a cranial nerve of the patient and to the electrical signal generator, providing at least a third electrode implanted within the patient's body and coupled to the electrical signal generator, generating a first electrical signal with the electrical signal generator, and delivering at least one electrical signal effective at the anode to block at least a sufficient portion of action potentials induced by the at least one electrical signal in the cranial nerve proximate the cathode to reduce a side effect of said induced action potentials.

In one aspect, the present invention relates to a system for treating a medical condition in a patient, comprising an electrical signal generator; a cathode and an anode operatively coupled to the electrical signal generator and a cranial nerve of the patient; and a third electrode operatively coupled to the electrical signal generator and implanted within the patient's body; wherein the electrical signal generator is capable of generating and delivering at least one electrical signal effective at the anode to block at least a sufficient portion of action potentials induced by the at least one electrical signal in the cranial nerve proximate the cathode to reduce a side effect of said induced action potentials.

In one aspect, the present invention relates to a method of treating a medical condition in a patient using an implantable medical device, comprising providing an electrical signal generator; coupling at least a first electrode and a second electrode to a cranial nerve of the patient and to the electrical signal generator; providing at least a third electrode implanted within the patient's body, wherein said third electrode is coupled to the electrical signal generator and not coupled to the cranial nerve; generating an electrical signal with the electrical signal generator, and applying the electrical signal: to the first electrode for a first time interval corresponding to a depolarization phase at a first region of said cranial nerve; to the second electrode for a second time interval corresponding to a hyperpolarization phase at a second region of said cranial nerve, wherein said second time interval exceeds said first time interval by a blocking time interval; and to the third electrode for a blocking time interval following said first time interval, wherein said blocking time interval is sufficient for said second electrode to block at the second region of said cranial nerve substantially all action potentials generated by the depolarization phase at the first region of said cranial nerve.

BRIEF DESCRIPTION OF THE DRAWINGS

The invention may be understood by reference to the following description taken in conjunction with the accompanying drawings, in which like reference numerals identify like elements, and in which:

FIGS. 6A-6C and FIGS. 7A-7C illustrate exemplary waveforms for capacitive-coupled (passive discharge) charge balancing of an electrical signal at a cathode, an anode, and a third electrode in accordance with an illustrative embodiment of the present invention; and FIGS. 8A-8C and FIGS. 9A-9C illustrate exemplary waveforms for active discharge charge balancing of an electrical signal at a cathode, an anode, and a third electrode in accordance with an illustrative embodiment of the present invention.

Figure 1A:
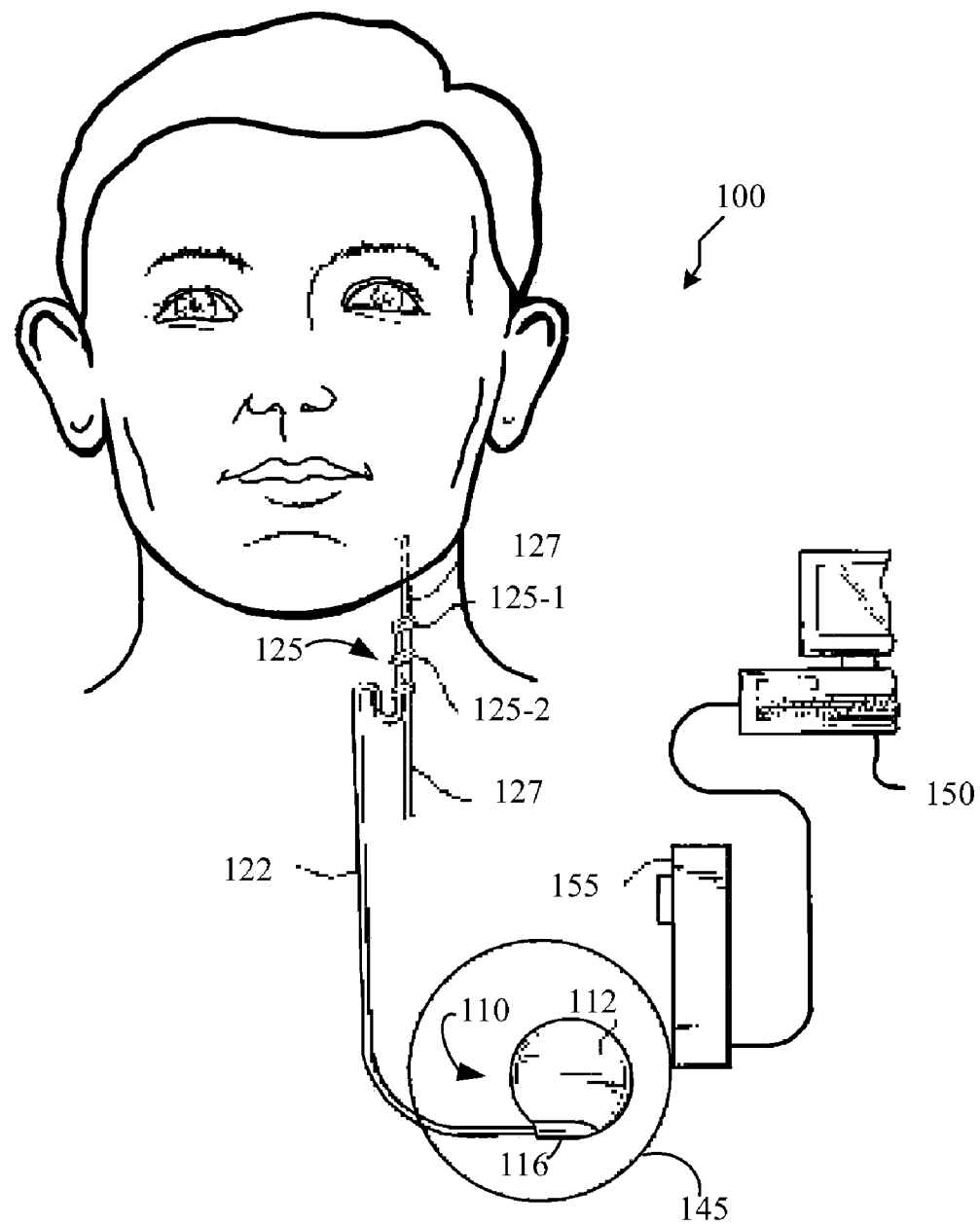
FIGS. 1A-1C provide stylized diagrams of an implantable medical device implanted into a patient's body for providing an electrical signal to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation, such as vagus nerve stimulation (VNS), has been proposed to treat a number of medical conditions pertaining to or mediated by one or more structures of the nervous system of the body, including epilepsy and other movement disorders, depression, anxiety disorders and other neuropsychiatric disorders, dementia, traumatic brain injury, coma, migraine headache, obesity, eating disorders (including obesity, anorexia nervosa, and bulimia nervosa), sleep disorders, cardiac disorders (such as congestive heart failure and atrial fibrillation), hypertension, endocrine disorders (such as diabetes and hypoglycemia), and pain syndromes (such as fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

Figure 1B:
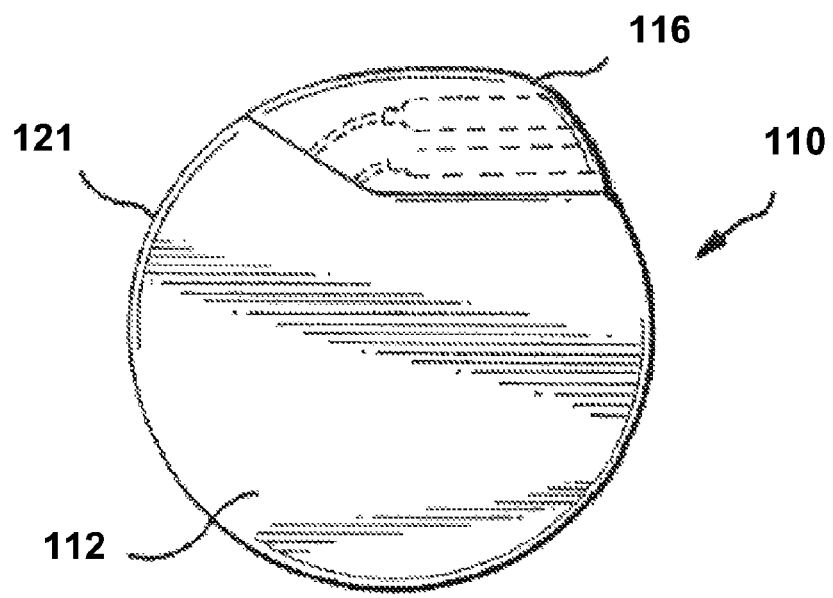
Figure 1C:
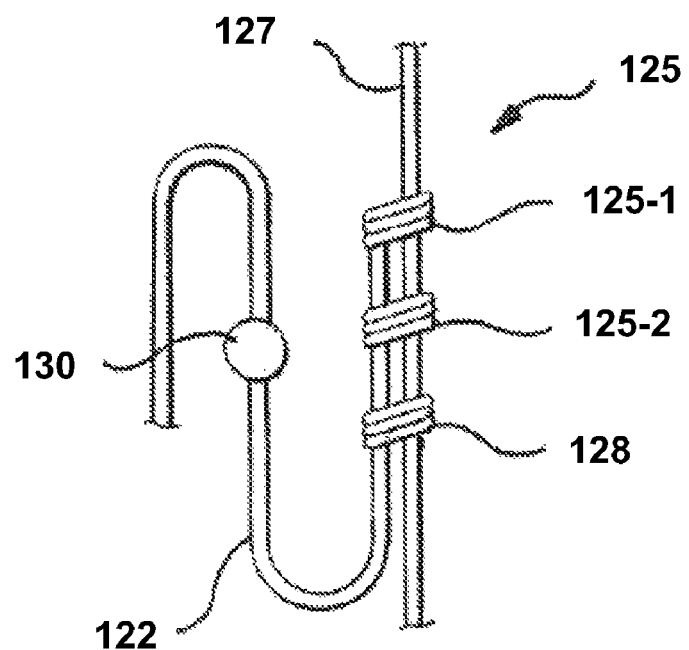

Although not so limited, a system capable of implementing embodiments of the present invention is described below. FIGS. 1A-1C depict a stylized implantable medical system 100 for implementing one or more embodiments of the present invention. FIGS. 1A-1C illustrate an electrical signal generator 110 having main body 112 comprising a case or shell 121 (FIG. 1B) with a header 116 (FIGS. 1A, 1B) for connecting to leads 122. The generator 110 is typically implanted in the patient's chest in a pocket or cavity formed by the implanting surgeon just below the skin (indicated by a line 145, FIG. 1A), similar to the implantation procedure for a pacemaker pulse generator.

A stimulating nerve electrode assembly 125, preferably comprising at least an electrode pair, is conductively connected to the distal end of an insulated, electrically conductive lead assembly 122, which preferably comprises a pair of lead wires (one wire for each electrode of an electrode pair). Lead assembly 122 is attached at its proximal end to connectors on the header 116 (FIG. 1B) on case 121. The electrode assembly 125 may be surgically coupled to a cranial nerve, such as vagus nerve 127 in the patient's neck or head or at another location, e.g., near the patient's diaphragm. Other cranial nerves, such as the trigeminal nerve and/or the glossopharyngeal nerve, may also be used to deliver the therapeutic electrical signal. The electrode assembly 125 preferably comprises a bipolar stimulating electrode pair 125-1, 125-2 (FIG. 1C), such as the electrode pair described in U.S. Pat. No. 4,573,481 issued Mar. 4, 1986 to Bullara. Suitable electrode assemblies are available from Cyberonics, Inc., Houston, Tex., USA as the Model 302 electrode assembly. However, persons of skill in the art will appreciate that many electrode designs could be used in the present invention, including unipolar electrodes. Returning to FIGS. 1A and 1C, the two electrodes are preferably wrapped about the cranial nerve (e.g., vagus nerve 127), and the electrode assembly 125 may be secured to the nerve by a spiral anchoring tether 128 (FIG. 1C) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue (FIG. 1C).

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1C), which may comprise two spiral loops of a three-loop helical assembly. The lead assembly 122 may comprise two distinct lead wires or a coaxial cable whose two conductive elements are respectively coupled to one of the conductive electrode ribbons. One suitable method of coupling the lead wires or cable to the electrodes 125-1, 125-2 comprises a spacer assembly such as that disclosed in U.S. Pat. No. 5,531,778, although other known coupling techniques may be used.

When an electrical signal is administered to the cranial nerve, at least one electrode will function as a cathode (i.e., charge will flow from the electrode into the cranial nerve) and at least one electrode will function as an anode (i.e., charge will flow from the cranial nerve into the electrode). In one embodiment, electrode 125-1 is the cathode and electrode 125-2 is the anode. Further, in a typical embodiment, the cathode 125-1 and the anode 125-2 are from about 5 mm apart to about 20 mm apart.

In another embodiment, electrode 125-1 is the anode and electrode 125-2 is the cathode.

The elastomeric body portion of each loop is preferably composed of silicone rubber, and the third loop 128 (which may or may not have an electrode) acts as the anchoring tether for the electrode assembly 125.

The IMD 100 according to the present invention also comprises a third electrode implanted in the patient's body. The third electrode can be coupled to a cranial nerve, such as the vagus nerve 127, or another cranial nerve, or it can be implanted elsewhere in the patient's body. In one embodiment, the third electrode is the case or shell 121 of the main body 112 of the electrical pulse generator 110. In one embodiment, the third electrode is coupled to the vagus nerve 127 below the branching off point of the recurrent laryngeal nerve. When the shell of the electrical signal generator is the third electrode, in a typical embodiment wherein the electrical signal generator is much larger in size than the cathode or the anode, the current density at the third electrode can be much lower than that at the cathode or the anode coupled to the nerve, and therefore the likelihood of biological impact proximate the shell of the electrical signal generator is also lower.

The IMD 100 according to the present invention may further comprise at least one fourth electrode and up to any desirable number of further electrodes. In one embodiment, the fourth electrode is operatively coupled to a cranial nerve and the electrical signal generator. It may be coupled to the vagus nerve 127. Alternatively, the fourth electrode is operatively coupled to the electrical signal generator and not to a cranial nerve.

The third electrode and the fourth and any additional electrodes can independently act as cathodes, anodes, or even both at different points in time, such as within a single pulse. Operation of the third electrode is exemplified in more detail below.

The electrical pulse generator 110 may be programmed with an external computer 150 using programming software of a type known in the art for stimulating neural structures, or other suitable software based on the description herein, and a programming wand 155 to facilitate radio frequency (RF) or other wireless communication between the computer 150 (FIG. 1A) and the pulse generator 110. The wand 155 and software permit wireless, non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A variety of stimulation therapies may be provided in IMD 100 of the present invention. Different types of nerve fibers (e.g., A, B, and C-fibers being different fibers targeted for stimulation) may respond differently to stimulation from electrical signals. More specifically, the different types of nerve fibers have different conduction velocities and stimulation thresholds and, therefore, differ in their responsiveness to stimulation. Certain pulses of an electrical stimulation signal, for example, may be below the stimulation threshold for a particular fiber and, therefore, may generate no action potential in the fiber. Thus, smaller or narrower pulses may be used to avoid stimulation of certain nerve fibers (such as C-fibers) having relatively high stimulation thresholds and target other nerve fibers (such as A and/or B fibers, which generally have lower stimulation thresholds and higher conduction velocities than C-fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long term stimulation.

In one embodiment, the pulse generator can deliver a biphasic, charge balanced electrical signal to the electrodes to reduce residual electrical charge at the eletrodes. A charge balancing pulse is typically delivered after an initial stimulation pulse in order to reduce the electrical charge at the stimulation electrode. For safe stimulation protocols, it is desirable to reduce the residual electrical charge after the stimulus pulse is delivered in order to minimize metal dissolution and pH changes at the electrode site. For a biphasic stimulus output, the charge at the electrodes can be balanced by reversing the current at the end of the first pulse so that the polarity of the second pulse is opposite that of the first pulse and the net charge is reduced to substantially zero. This can be accomplished by delivery of the stimulus current from the pulse generator through either an active discharge mode (of which exemplary waveforms are shown in FIGS. 8-9) or by a capacitive coupling mode (of which exemplary waveforms are shown in FIGS. 6-7). In the active discharge mode, the pulse generator delivers a first stimulus pulse of specified polarity and a second charge balancing pulse of an opposite polarity so that the charge in the first pulse phase is equal to the second pulse phase to give a substanitially net zero charge. In the capacitive coupling mode, the pulse generator delivers a first pulse of specified polarity. At the end of the first pulse a switch is activated in the output circuitry of the pulse generator to reverse the current flow through a capacitor circuit to passively dissipate the charge that was delivered in the first pulse. The reversal of current causes an opposite polarity of the second phase as compared to the first phase; the end effect resulting in a reduction in the electrical charge at the electrode.

The term "cathode" in the context of biphasic stimulation refers to the electrode functioninig as a cathode in the first pulse referred to above.

In addition or alternatively to biphasic stimulation, the signal output parameters of the pulse generator can be programmed or adjusted to deliver other output waveforms such as monophasic or multiphasic. The pulse generator output parameters can include adjustable pulse durations and pulse amplitudes for each phase as well as an adjustable time interval between the initial pulse and the subsequent charge balancing pulse. The charge balancing pulse may be delivered at predefined periods during a stimulation interval. For example, when the stimulation pulses are close together in duration such as in a high frequency burst, there may not be sufficient time to deliver a charge balancing pulse after every stimulation pulse. In this case the charge balancing pulse can be delivered at the end of the high frequency burst.

If charge balancing is performed, by either passive discharge or active discharge, in one embodiment, the passive discharge or the active discharge can be performed at at least one electrode selected from the group consisting of the cathode and the anode. In a further embodiment, the passive discharge or active discharge is performed at both the cathode and the anode.

As used herein, the terms "stimulation," "stimulate," and their variants may generally refer to delivery of a signal, stimulus, or impulse to neural tissue for affecting neuronal activity of a neural tissue (e.g., a volume of neural tissue in the brain or a nerve). The effect of such stimulation on neuronal activity is termed "modulation"; however, for simplicity, the terms "stimulating" and "modulating", and variants thereof, are sometimes used interchangeably herein. The effect of delivery of the stimulation signal to the neural tissue may be excitatory or inhibitory and may potentiate acute and/or long-term changes in neuronal activity. For example, the effect of "stimulating" or "modulating" a neural tissue may comprise one or more of the following effects: (a) changes in neural tissue to initiate an action potential (bi-directional or unidirectional); (b) inhibition of conduction of action potentials (endogenous or externally stimulated) or blocking the conduction of action potentials (hyperpolarizing or collision blocking), (c) affecting changes in neurotransmitter/neuromodulator release or uptake, and (d) changes in neuro-plasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization.

According to an exemplary method of the present invention, the IMD 100 provides electrical signal therapy that comprises generating a first electrical signal with the electrical signal generator 110, and delivering at least one electrical signal effective at the anode 125-2 to block at least a sufficient portion of action potentials induced by the at least one electrical signal in the cranial nerve proximate the cathode 125-1 to reduce a side effect of said induced action potentials. In one embodiment, the electrical signal may be effective at the anode 125-2 to block substantially all of the exogenously induced action potentials. The at least one electrical signal may also be effective at the anode 125-2 to block at least a portion of endogenous action potentials.

The portion of the action potentials induced by the at least one electrical signal in the cranial nerve proximate the cathode which are blocked by performance of the method can be in any class of nerve fibers, e.g., A fibers, B fibers, C fibers, or any combination thereof. In one embodiment, at least a portion of the action potentials are blocked in B fibers having an action potential conduction velocity from about 3 m/sec to about 15 m/sec.

Whether afferent or efferent action potentials are blocked will depend on the orientation of the cathode and the anode. In the embodiment of FIG. 1, wherein the cathode 125-1 is closer to the brain than the anode 125-2, the blocked action potentials are efferent action potentials. In a further embodiment, the blocked efferent action potentials are action potentials that would, if unblocked, stimulate muscle activity proximate the larynx. If substantially unblocked, such muscle activity could give rise to vocal cord modulation and affect the quality, volume, timbre, or other properties of the patient's voice. In another further embodiment, the blocked efferent action potentials are action potentials that could, if substantially unblocked, cause side effects such as shortness of breath, apnea, or dsypnea. In one particular embodiment, the side effect is selected from the group consisting of vocal cord modulation, breathing difficulty, shortness of breath, apnea, and dsypnea.

The invention is not limited to any particular process or technique, so long as the electrical signal is effective at the anode 125-2 to block at least a sufficient portion of action potentials induced by the at least one electrical signal in the cranial nerve proximate the cathode 125-1 to reduce a side effect of said induced action potentials. In one exemplary embodiment, the electrical signal generator 110 is capable of generating and delivering both: (1) a first electrical signal to both the cathode and the anode in a first time period, wherein the first electrical signal depolarizes the cranial nerve proximate the cathode and hyperpolarizes the cranial nerve proximate the anode; and (2) a second electrical signal to both the anode and the third electrode in a second time period following the first time period, wherein the second electrical signal hyperpolarizes the cranial nerve proximate the anode for a duration sufficient to block at least a sufficient portion of action potentials induced by the at least one electrical signal in the cranial nerve proximate the cathode to reduce a side effect of said induced action potentials. One example of waveforms that can effect the depolarization and hyperpolarization of this embodiment, which can be used when the third electrode is the shell of the electrical signal generator, is shown in FIG. 6. A second example of such waveforms, wherein the second time period does not immediately follow the first time period, is shown in FIG. 7. FIGS. 8-9 show waveforms suitable in an embodiment wherein active charge balancing is performed.

In one desirable embodiment, the net charge on the cathode, the anode, the third electrode, and any additional electrode is substantially zero.

In this embodiment, the duration of depolarization proximate the cathode can be from about 0.01 msec to about 1 msec and the duration of hyperpolarization proximate the anode can be from about 0.05 msec to about 5 msec.

In another embodiment, not shown in the figures, blocking at least a sufficient portion of action potentials induced by the at least one electrical signal in the cranial nerve proximate the cathode to reduce a side effect of said induced action potentials can be performed by generating and delivering both: (1) a first electrical signal to both the cathode and the anode in a first time period, wherein the first electrical signal depolarizes the cranial nerve proximate the cathode and hyperpolarizes the cranial nerve proximate the anode; and (2) a second electrical signal to both the anode and the third electrode in a second time period following the first time period, wherein the second electrical signal is a current alternating at the anode with a sufficient amplitude and frequency and for a duration sufficient to block at least a portion of action potentials induced by the at least one electrical signal in the cranial nerve proximate the cathode (not shown). The ability of an alternating current at a sufficient frequency, such as about 20 KHz or greater, to block action potentials is discussed by Campbell and Woo, *Bull. L.A. Neurolog. Soc.* 31(2):87-94 (1964), which is hereby incorporated by reference. Persons of skill in the art will appreciate that much lower frequencies, e.g., 200 Hz or even lower in some instances, may be sufficient to block action potentials on some cranial nerves.

A "pulse" is used herein to refer to a single application of electrical charge from the cathode to the cranial nerve. Individual pulses are separated by a time period in which no charge is delivered to the nerve, which can be called the "interpulse interval." A "burst" is used herein to refer to a plurality of pulses, wherein no charge is delivered to the nerve before the first pulse of the burst for a time period at least twice as long as the interpulse interval and no charge is delivered to the nerve after the last pulse of the burst for a time period at least twice as long as the interpulse interval. The time period between the end of the last pulse of a first burst and the initiation of the first pulse of the next subsequent burst can be called the "interburst interval." In one embodiment, the interburst interval is at least 100 msec.

A plurality of pulses can refer to any of (a) a number of consecutive pulses within a burst, (b) all the pulses of a burst, or (c) a number of consecutive pulses including the final pulse of a first burst and the first pulse of the next subsequent burst.

Typical cranial nerve stimulation can be performed with an interpulse frequency of 20-30 Hz (resulting in a number of pulses per burst of 140-1800, at a burst duration from 7-60 sec). In one embodiment, at least one of the first electrical signal, the second electrical signal, and the third electrical signal delivers microbursts. Microburst neurostimulation is discussed by U.S. Ser. No. 11/693,451, filed Mar. 2, 2007 and published as United States patent Publication No. 20070233193, and incorporated herein by reference. In one embodiment, at least one of the first electrical signal, the second electrical signal, and the third electrical signal is characterized by having a number of pulses per microburst from 2 pulses to about 25 pulses, an interpulse interval of about 2 msec to about 50 msec, an interburst period of at least 100 msec, and a microburst duration of less than about 1 sec, such as less than about 100 msec.

As stated above, different fiber types of cranial nerves propagate action potentials at different velocities. Specifically, the nerve fiber types generally recognized in the art, along with some of their typical properties, are shown in the following table:

| Mammalian Axon Properties | | | |
| --- | --- | --- | --- |
| Fiber Types | Fiber Diameter (μm) | Conduction Velocity (m/sec) | Action Potential Duration (msec) |
| Aα | 12-22 | 70-100 | 0.4-0.5 |
| Aβ | 5-13 | 30-70 | 0.4-0.5 |
| Aγ | 3-8 | 15-40 | 0.4-0.7 |
| Aδ | 1-5 | 12-30 | 0.2-1.0 |
| B | 1-3 | 3-15 | 1.2 |
| C (unmyelinated) | 0.2-1.2 | 0.2-2.0 | 2 |

In one embodiment, the sufficient portion of blocked action potentials are blocked in one or more nerve fiber types selected from the group consisting of Aα fibers, Aβ fibers, Aγ fibers, Aδ fibers, B fibers, and C fibers.

Figure 2:
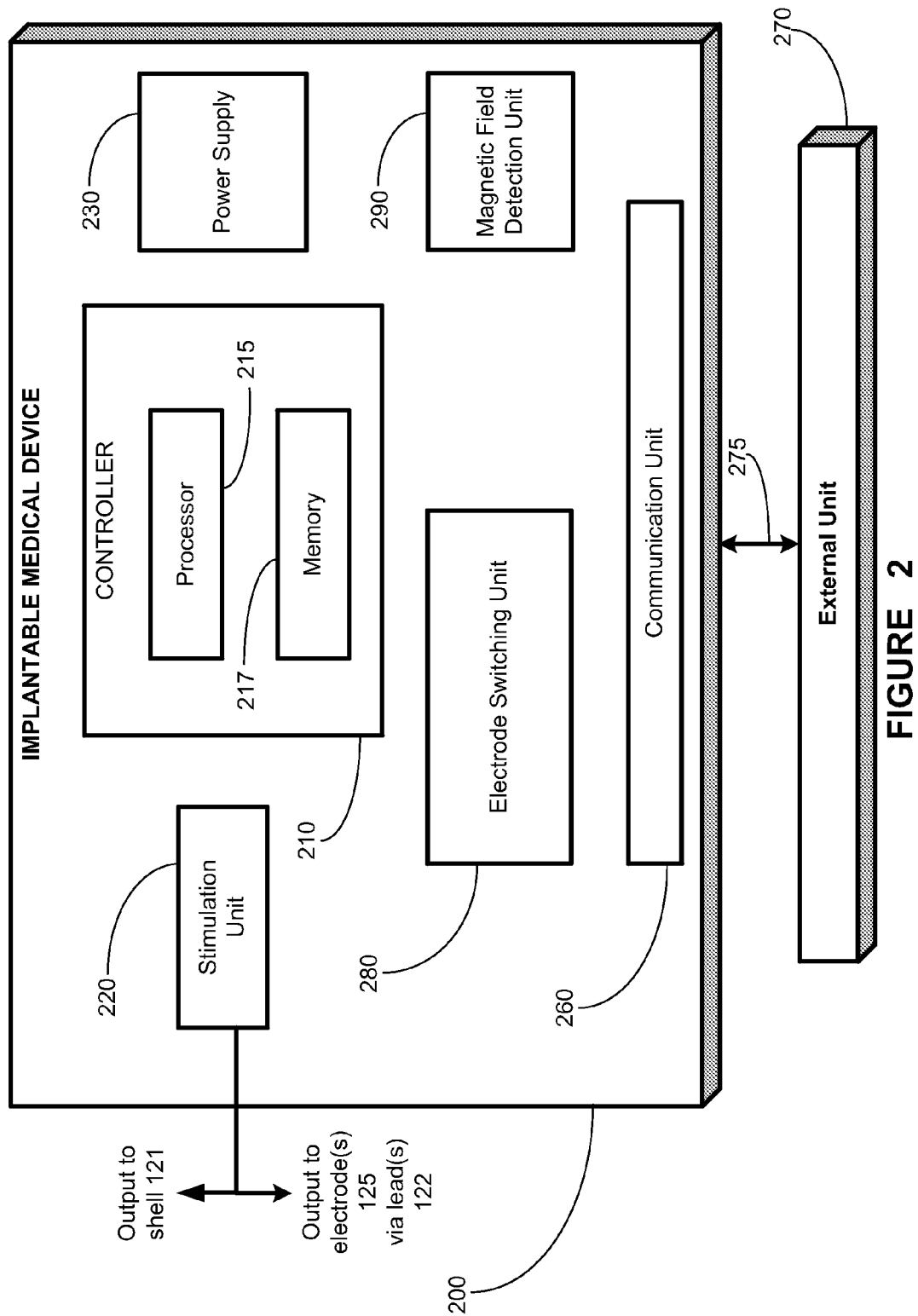
FIG. 2 illustrates a block diagram depiction of the implantable medical device of FIG. 1, in accordance with one illustrative embodiment of the present invention.

Turning now to FIG. 2, a block diagram depiction of an implantable medical device, in accordance with one illustrative embodiment of the present invention is illustrated. The IMD 200 may be coupled to various leads, e.g., 122 (FIGS. 1A, 1C). Stimulation signals used for therapy may be transmitted from the IMD 200 to target areas of the patient's body, specifically to various electrodes associated with the leads 122. Stimulation signals from the IMD 200 may be transmitted via the leads 122 to stimulation electrodes (electrodes that apply the therapeutic electrical signal to the target tissue) associated with the electrode assembly 125, e.g., 125-1, 125-2 (FIG. 1A). Further, signals from sensor electrodes (electrodes that are used to sense one or more body parameters such as heart rate, heart rate variability, temperature, rate of change of temperature, blood pressure, brain activity, etc.) may also be communicated to the IMD 200.

The IMD 200 may comprise a controller 210 capable of controlling various aspects of the operation of the IMD 200. The controller 210 is capable of receiving internal data and/or external data and controlling the generation and delivery of a stimulation signal to target tissues of the patient's body. For example, the controller 210 may receive manual instructions from an operator externally, or may perform stimulation based on internal calculations and programming. The controller 210 is capable of affecting substantially all functions of the IMD 200.

The controller 210 may comprise various components, such as a processor 215, a memory 217, etc. The processor 215 may comprise one or more micro controllers, micro processors, etc., that are capable of executing a variety of software components. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical signals to one or more electrodes via leads. The stimulation unit 220 is capable of delivering a programmed, primary mode electrical signal to the leads 122 coupled to the IMD 200. The electrical signal may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed. In one embodiment, the stimulation unit 220 is also capable of delivering a programmed electrical signal to the shell 121 of the electrical pulse generator 110.

The IMD 200 may also comprise an electrode switching unit 280. The electrode switching unit 280 is capable of selecting the destination electrodes to which an electrical signal is delivered, and can also be capable of changing the polarity of the destination electrodes as well. Particular embodiments of the electrode switching unit 280 are shown in more detail in FIG. 3 and FIG. 4. In preferred embodiments, the electrode switching unit is capable of selecting the destination electrodes rapidly, i.e., in about 10 microseconds or less, and in any event at a sufficiently rapid rate to permit destination electrodes to be selected in a time such that the cranial nerve proximate the anode 125-2 remains hyperpolarized until changing of the destination electrodes is completed. However, embodiments in which the cranial nerve proximate the anode 125-2 does not remain hyperpolarized during selection of the destination electrodes are within the scope of the invention.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230, may comprise a lithium/thionyl chloride cell or a lithium/carbon monofluoride (LiCFx) cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

In one embodiment, the communication unit 260 can transmit a log of stimulation data to the patient, a physician, or another party.

The IMD 200 is capable of delivering stimulation that can be intermittent, periodic, random, sequential, coded, and/or patterned. The stimulation signals may comprise an electrical stimulation frequency of approximately 0.1 to 2500 Hz. The stimulation signals may comprise a pulse width in the range of approximately 1-2000 micro-seconds. The stimulation signals may comprise current amplitude in the range of approximately 0.1 mA to 10 mA. The stimulation delivered by the IMD 200 according to its programming may be referred to herein as "normal operations" or as a "normal operating mode."

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field. The stimulation comprising blocking of exogenous action potentials at the anode, as described herein, may be activated, deactivated, or alternatively activated or deactivated using a magnetic input.

The magnetic field detection unit 290 may comprise various sensors, such as a Reed Switch circuitry, a Hall Effect sensor circuitry, and/or the like. The magnetic field detection unit 290 may also comprise various registers and/or data transceiver circuits that are capable of sending signals that are indicative of various magnetic fields, the time period of such fields, etc. In this manner, the magnetic field detection unit 290 is capable of detecting whether the detected magnetic field relates to an inhibitory input or an excitatory input from an external source. The inhibitory input may refer to an inhibition of, or a deviation from, normal stimulation operation. The excitatory input may refer to additional stimulation or deviation from normal stimulation.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, one or more of the circuitry and/or software units associated with the various blocks illustrated in FIG. 2 may be combined into a programmable device, such as a field programmable gate array, an ASIC device, etc.

Figure 3:
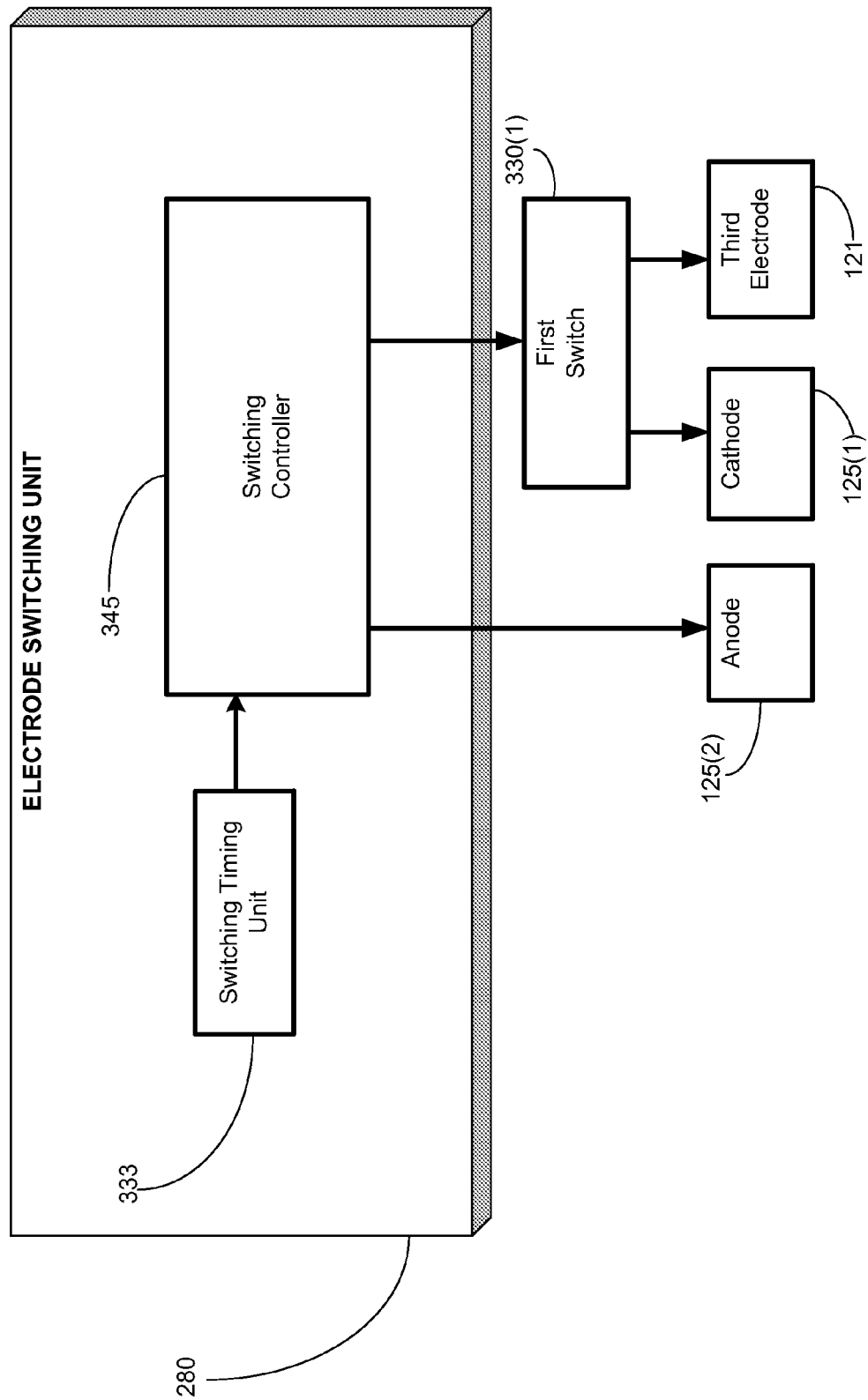
FIG. 3 illustrates a block diagram depiction of an electrode switching unit, in accordance with one illustrative embodiment of the present invention.
Figure 4:
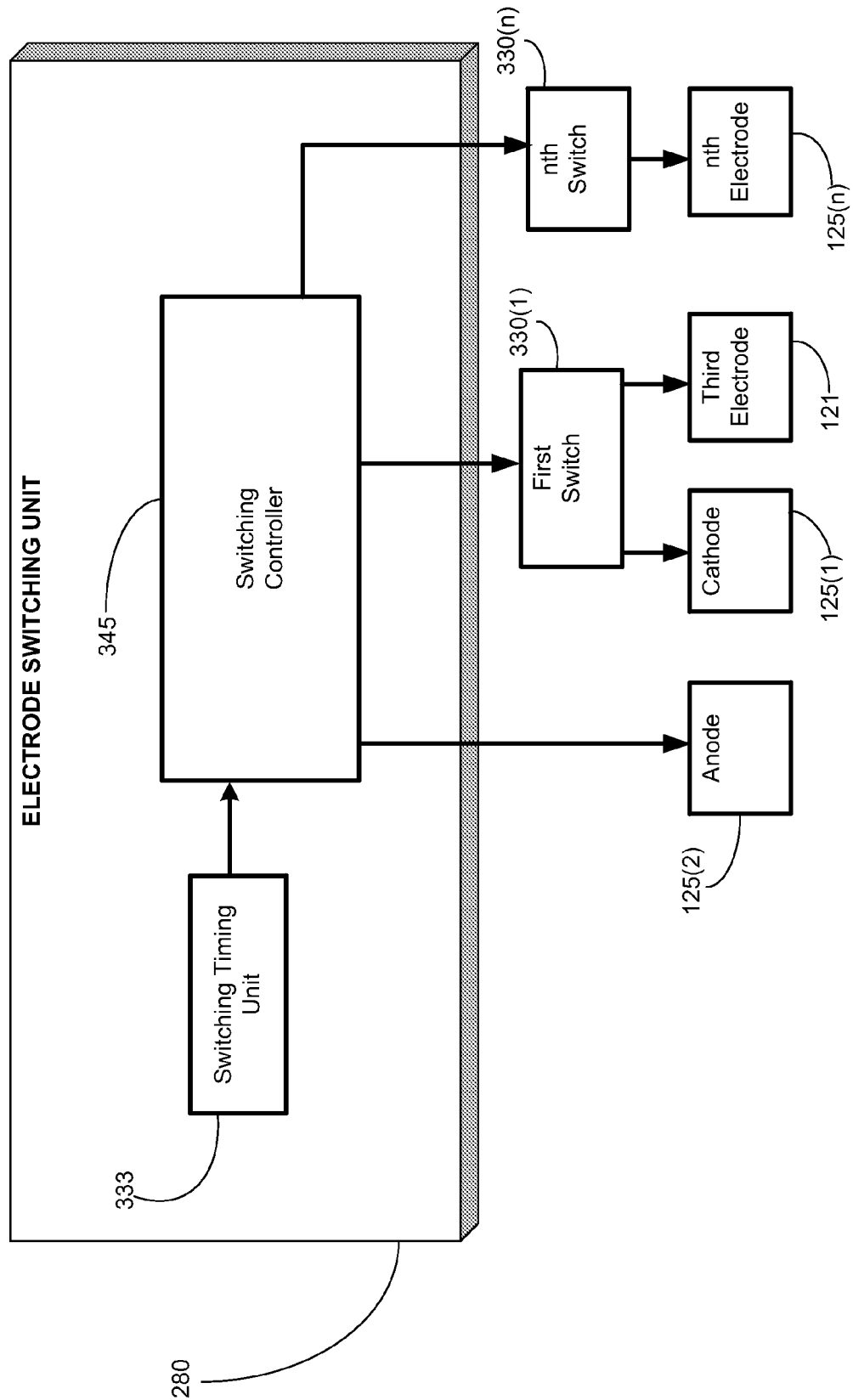
FIG. 4 illustrates a block diagram depiction of an electrode switching unit, in accordance with one illustrative embodiment of the present invention.

FIG. 3 shows in greater detail the electrode switching unit 280 (FIG. 2). The electrode switching unit 280 comprises a switching controller 345. The switching controller 345 transmits signals to one or more switches, generically, n switches, of which one switch 330(1) is shown. Switch 330(1) effects switching between two or more destination electrodes, in this embodiment, the cathode 125(1) and the third electrode (shell 121). Although FIG. 3 shows one switch 330(1) and three electrodes 125-1, 125-2, and 121, the person of ordinary skill in the art having the benefit of the present disclosure will understand that the number of switches 330 and their connections with the various electrodes 125, 121, etc. can be varied as a matter of routine optimization. For example, FIG. 4 shows another embodiment of the electrode switching unit 280, comprising an nth switch 330(n) and an nth electrode 125(n). A switching timing unit 333 can signal to the switching controller 345 that a desired time for switching between destination electrodes has been reached.

Instructions for implementing one or a series of predetermined and/or programmable stimulation regimens may be stored in the IMD 200. In one embodiment, each of a plurality of stimulation regimens may respectively relate to a particular disorder or side effect of treatment. In one embodiment, different regimens relating to the same side effect may be implemented to increase or decrease side effects of stimulation, such as activation of muscles, e.g., muscles proximate the larynx, relative to such side effects at previous times. For example, a regimen comprising sufficient blocking of exogenous action potentials at the anode to reduce a side effect of said exogenous action potentials can be performed during a selected time period when the side effect is likely to be especially pronounced.

In another embodiment, different regimens relating to the same side effect may be implemented upon qualitative or quantitative detection of, e.g., abduction or adduction of the vocal cords or muscle activity proximate the larynx. Such detection could be performed by electromyography or other appropriate techniques, such as those disclosed in Baker, Jr., U.S. Pat. No. 5,205,285.

The switching controller 345 may be a processor that is capable of receiving data relating to the stimulation regimens. In an alternative embodiment, the switching controller may be a software or a firmware module. Based upon the particulars of the stimulation regimens, the switching timing unit 333 may provide timing data to the switching controller 345. The switches 330 may be electrical devices, electromechanical devices, and/or solid state devices (e.g., transistors).

Figure 5:
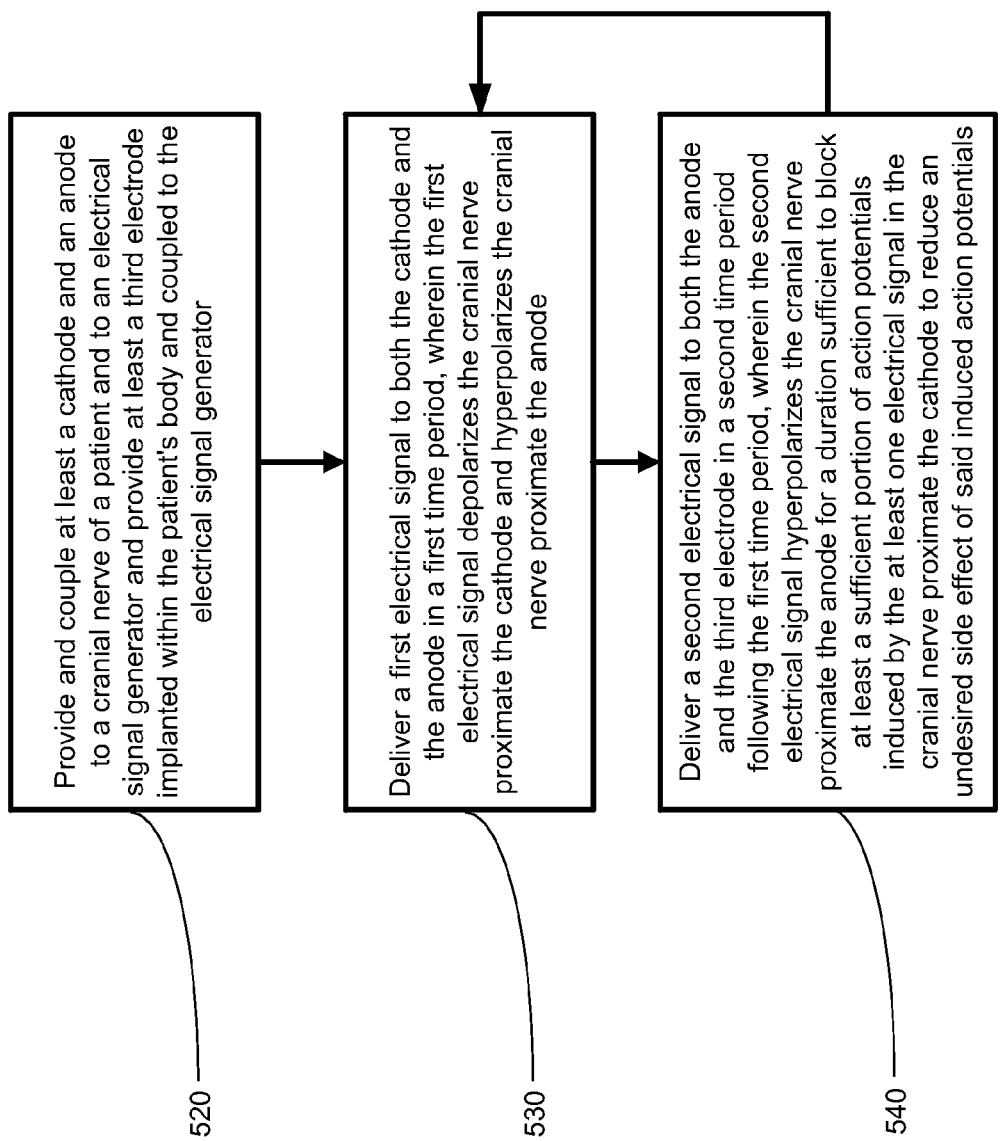
FIG. 5 illustrates a flowchart depiction of a method in accordance with an illustrative embodiment of the present invention.

FIG. 5 shows one embodiment of a method of sufficiently blocking exogenous action potentials at the anode to reduce a side effect of said exogenous action potentials according to the present invention. In this embodiment, as shown in step 520, the method includes providing a cathode, an anode, and at least a third electrode as described above, and coupling the cathode, the anode, and the third electrode to an electrical signal generator. The method also includes providing 530 a first electrical signal to both the cathode and the anode in a first time period, wherein the first electrical signal depolarizes the cranial nerve proximate the cathode and hyperpolarizes the cranial nerve proximate the anode. Thereafter, the method comprises delivering 540 a second electrical signal to both the anode and the third electrode in a second time period following the first time period, wherein the second electrical signal hyperpolarizes the cranial nerve proximate the anode for a duration sufficient to block at least a sufficient portion of action potentials induced by the at least one electrical signal in the cranial nerve proximate the cathode to reduce a side effect of said induced action potentials.

In the method shown in FIG. 5, delivery 540 can occur immediately (i.e., less than 10 microseconds, including zero time difference) after delivery 530, or it can occur after a delay of greater than 10 microseconds. Preferably, the delay is short enough that the cranial nerve proximate the anode remains hyperpolarized until delivery 540 is performed.

In the methods shown in FIG. 5, one or more of the properties of the first electrical signal and the second electrical signal can differ, or all the properties can remain the same. (The terms "first electrical signal" and "second electrical signal" are chosen for convenience and are not to be construed as requiring the electrical signals to be separated in time or space or differ in any properties, except as expressly described herein).

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. An implantable medical device to treat a medical condition in a patient, the implantable medical device comprising:
   a cathode and an anode configured to be coupled to an electrical signal generator and to be coupled to a cranial nerve of the patient;
   a third electrode configured to be implanted within the patient and configured to be coupled to the electrical signal generator;
   wherein the electrical signal generator is configured to deliver a first electrical signal to the cathode and to the anode during a first time period, wherein the first electrical signal causes depolarization of a first portion of the cranial nerve proximate to the cathode and causes hyperpolarization of a second portion of the cranial nerve proximate to the anode, and
   wherein the electrical signal generator is configured to deliver a second electrical signal to the anode and to the third electrode during a second time period following the first time period, wherein the hyperpolarization of the second portion of the cranial nerve caused by the first electrical signal persists when the second electrical signal is delivered and delivery of the second electrical signal continues the hyperpolarization of the second portion of the cranial nerve.

2. The implantable medical device of claim 1, wherein delivery of the second electrical signal is effective to inhibit one or more side effects associated with depolarization of the first portion of the cranial nerve.

3. The implantable medical device of claim 2, wherein the one or more side effects include at least one of vocal cord modulation, breathing difficulty, shortness of breath, apnea, dyspnea, and impairment of at least one quality of the patient's voice.

4. The implantable medical device of claim 1, wherein the third electrode is not coupled to the cranial nerve.

5. The implantable medical device of claim 1, wherein the third electrode is a shell of the electrical signal generator.

6. The implantable medical device of claim 1, wherein the cranial nerve is a vagus nerve.

7. The implantable medical device of claim 5, wherein current density associated with at least one of the first electrical signal and the second electrical signal proximate the third electrode is reduced relative to a corresponding current density proximate the anode and the cathode.

8. A method of treating a medical condition in a patient using an implantable medical device, the method comprising:
delivering a first electrical signal during a first time period to a cathode and an anode of the implantable medical device, wherein the implantable medical device is coupled to a cranial nerve of the patient, wherein the first electrical signal causes depolarization of a first portion of the cranial nerve proximate to the cathode and causes hyperpolarization of a second portion of the cranial nerve proximate to the anode, and
delivering a second electrical signal to the anode and to a third electrode of the implantable medical device during a second time period following the first time period, wherein the hyperpolarization of the second portion of the cranial nerve caused by the first electrical signal persists when the second electrical signal is delivered and delivery of the second electrical signal continues the hyperpolarization of the second portion of the cranial nerve.

9. The method of claim 8, wherein the hyperpolarization of the second portion of the cranial nerve during the first time period and during the second time period is effective to block at least a portion of endogenous action potentials at the second portion of the cranial nerve and to block at least a portion of action potentials induced by the depolarization caused by the first electrical signal.

10. The method of claim 8, wherein the depolarization of the first portion of the cranial nerve induces action potentials at the first portion of the cranial nerve, wherein the action potentials are inhibited, by the hyperpolarization of the second portion of the cranial nerve, from propagating in one or more nerve fiber types of the cranial nerve, wherein the one or more nerve fiber types include at least one of Aα fibers, Aβ fibers, Aγ fibers, Aδ fibers, B fibers, and C fibers.

11. The method of claim 10, wherein the action potentials are efferent action potentials.

12. The method of claim 8, wherein the third electrode is a shell of the implantable medical device.

13. The method of claim 8, wherein delivery of the second electrical signal is effective to block action potentials that would, if unblocked, propagate towards one or more body structures of the patient that are innervated by the cranial nerve, the blocking of the action potentials reducing one or more side effects occurring at the one or more body structures of the patient.

14. The method of claim 8, wherein a duration of the depolarization proximate to the cathode is from about 0.01 msec to about 1 msec.

15. The method of claim 8, further comprising balancing charge by passive discharge from at least one of the cathode and the anode.

16. The method of claim 15, wherein passive discharge is performed at both the cathode and the anode.

17. The method of claim 8, further comprising balancing charge by active discharge from at least one of the cathode and the anode.

18. The method of claim 17, wherein active discharge is performed at both the cathode and the anode.

19. A method comprising:
delivering a first electrical signal during a first time period to an anode and a cathode of an implantable medical device coupled to a cranial nerve of a patient, wherein the first electrical signal causes depolarization of a first portion of the cranial nerve proximate to the cathode and causes hyperpolarization of a second portion of the cranial nerve proximate to the anode, and
delivering a second electrical signal to the anode and to a third electrode of the implantable medical device during a second time period following the first time period, wherein the hyperpolarization of the second portion of the cranial nerve caused by the first electrical signal persists when the second electrical signal is delivered, and wherein delivery of the second electrical signal is effective to block action potentials that would, if unblocked, stimulate muscle activity proximate to a larynx of the patient.

20. A system comprising:
a cathode and an anode configured to be coupled to an electrical signal generator and to be coupled to a cranial nerve of a patient;
an electrode configured to be implanted within the patient and to be coupled to the electrical signal generator;
wherein the electrical signal generator is configured to deliver a first electrical signal to the anode and the cathode during a first time period, wherein the first electrical signal causes depolarization of a first portion of the cranial nerve proximate to the cathode and causes hyperpolarization of a second portion of the cranial nerve proximate to the anode;
wherein the electrical signal generator is configured to deliver a second electrical signal to the anode and to the electrode during a second time period following the first time period, wherein the hyperpolarization of the second portion of the cranial nerve caused by the first electrical signal persists when the second electrical signal is delivered, and wherein delivery of the second electrical signal is effective to block action potentials that would, if unblocked, stimulate muscle activity proximate to a larynx of the patient.

21. The system of claim 20, further comprising a switching controller to control delivery and duration of the first electrical signal to the anode and the cathode, and to control delivery and duration of the second electrical signal to the anode and the electrode.

* * * * *